United States Patent [19]

Okada et al.

[11] Patent Number: 5,094,939
[45] Date of Patent: Mar. 10, 1992

[54] CHEMILUMINESCENCE ASSAYS USING STABILIZED DIOXETANE DERIVATIVES

[75] Inventors: Masahisa Okada; Yoshihiro Ashihara; Tadashi Ninomiya; Akira Yano, all of Tokyo, Japan

[73] Assignee: Fujirebio, Inc., Tokyo, Japan

[21] Appl. No.: 382,112

[22] Filed: Jul. 19, 1989

[30] Foreign Application Priority Data

Jul. 19, 1988 [JP] Japan .................. 63-178193
Jul. 19, 1988 [JP] Japan .................. 63-178194

[51] Int. Cl.$^5$ .................. C12Q 1/68; C12Q 1/42; G01N 21/76
[52] U.S. Cl. .................. 435/6; 435/7.9; 435/19; 435/21; 436/172; 436/800; 436/805
[58] Field of Search .................. 435/7, 19, 6, 21, 7.9; 436/172, 800, 805

[56] References Cited

U.S. PATENT DOCUMENTS 4,778,755  10/1988  Tsay et al. .................. 435/21

FOREIGN PATENT DOCUMENTS 254051  1/1988  European Pat. Off. .
8800695  1/1988  PCT Int'l Appl. .

OTHER PUBLICATIONS

Schaap, A. P., et al., *Tet. Letters*, 28:935 (1987).
Schaap, A. P., et al., *Tet. Letters*, 28:1159 (1987).
Bronstein, I. Y., et al., *Clin. Chem.*, 35(9):1441 (1989).

*Primary Examiner*—Esther L. Kepplinger
*Assistant Examiner*—Toni R. Scheiner
*Attorney, Agent, or Firm*—Oblon, Spivak, McClelland, Maier & Neustadt

[57] ABSTRACT

A multi-pH chemiluminescence-based assay method comprising first-stage light production by the activation by cleavage of a phosphatase cleavable dioxetane derivative within a pH range optimal for enzyme catalysis, followed by the second-stage generation of increased light energy from the products of enzyme-catalyzed cleavage of the dioxetane derivative by the adjustment of the pH to a strongly alkaline pH optimal for the generation of light energy. The assay method is suitable for both solution phase and solid state assay formats. Light generation enhancers can be used further to increase the light yield.

11 Claims, 3 Drawing Sheets

CHEMILUMINESCENCE ASSAYS USING STABILIZED DIOXETANE DERIVATIVES

BACKGROUND OF THE INVENTION

1. Field of the Invention

This invention relates to a novel method of conducting chemiluminescence-based assays. More particularly, this invention relates to chemiluminescence-based assays in an aqueous environment in which a first, light-producing, enzymatic reaction is carried out at a pH at which an enzyme is active and using as a substrate an enzyme-cleavable dioxetane derivative, and carrying out a second light-producing reaction under strongly alkaline conditions to generate visible light as a sustained glow of greater intensity than that generated in the first light-producing reaction.

2. Description of Prior Art

Chemical and biochemical assays in which the presence or concentration, or both, of an analyte is measured by luminescence assays are based on either chemiluminescent or bioluminescent reactions, and are commonly utilized as highly sensitive methods of ultramicroanalysis. Such prior art methods of chemiluminescence assay include: (1) $H_2H_2$ measurement with luminol/potassium ferricyanide in the presence of an alkali [Bostick et al., Anal. Chem. 47:447–451 (1975)]; (2) glucose measurement with luminol-glucose oxidase [Bostick et al., 1975]; and (3) hemoglobin measurement with luminol/$H_2H_2$ in the presence of an alkali [Ewetz, L. et al., Anal. Biochem., 71:564–570 (1976)]; (4) ATP measurement with *Photinus pyralis* luciferin-luciferase [Addanki et al., Anal. Biochem., 14:261-264 (1966)]; (5) measurement of intracellular free calcium ions with aequorin [Blinks et al., Pharmacol. Rev., 28:1-93 (1976)]; and (6) NADH measurement with bacterial luciferase [Hasting, J.W. et al., Ann. Rev. Microbiol., 31:549 (1977)].

These conventional methods of chemiluminescence assays described exhibit several problems. Method (1) is incapable of precise measurements; either the sample itself is decomposed by the oxidizer used to produce luminescence or the oxidizer itself is decomposed. Method (2) is difficult to carry out in aqueous systems; the reagents used to produce luminescence are poorly soluble in water and hence are not suitable for bioassays. Method (3) involves an intermittent luminescent reaction, and requires considerable skill in achieving timed measurements. Methods (4)–(6) require the use of more expensive enzymes than those used in the assays of the present invention, enzymes which are also inactivated to a large extent during immunoassays.

Previous methods of detecting a substance using enzymatically-induced decomposition of enzyme cleavable dioxetane derivatives [Bronstein, WO 88/00695, published Jan. 28, 1988; Schaap, A.P., et al., Tetrahedron Lett, 28:1155 (1982)] have been conducted at pH values which were most suitable for enzyme activity. Although the sensitivities of biochemical assays based upon the aforementioned principle were much greater and more efficient than those previously obtained with the luminescence-based assays such as those cited above, the sensitivities were limited to those produced at the pH values optimal for enzyme activity.

SUMMARY OF THE INVENTION

It has now been discovered that in chemiluminescence assays using as reporter molecules enzyme-activatable chemiluminescent dioxetanes, e.g., those of formulae (I) and (II) below, greater sensitivity, precision and efficiency, and enhanced production of light energy, can be achieved by carrying out the assay in two stages. The first stage is conducted within a pH range at which enzyme-catalyzed cleavage (i.e., activation) of an enzyme-cleavable substituent on the dioxetane molecule occurs, and produces visible light in the form of a sustained glow. The second stage is carried out at an alkaline pH optimal for the generation of visible light from the products of the first stage's enzymatic cleavage of the reporter molecules. This light is also generated as a sustained glow, but is of a greater intensity than the light generated by the first stage's enzymatic cleavage reaction.

It is, therefore, an object of this invention to provide a novel method of conducting chemiluminescence-based assays.

It is also an object of this invention to provide a novel method of conducting chemical and biochemical assays in which the presence or concentration, or both, of an analyte is measured by luminescence.

A further object of this invention is to provide multi-pH chemiluminescence-based assay methods suitable for use in an aqueous environment.

A still further object of this invention to provide multi-pH chemiluminescence-based assay methods using pH values optimal for enzyme-catalyzed reactions leading to the activation of chemiluminescent molecules and pH values optimal for light energy production from enzyme-decomposed chemiluminescent molecules.

It is still another object of the invention to provide both soluble phase and solid phase assays incorporating the multi-pH assay steps of this invention.

These and other objects, as well as the nature, scope and utilization of this invention, will become apparent to those skilled in the art from the following description, the drawings and the appended claims.

DETAILED DESCRIPTION OF THE INVENTION

Figure 1:
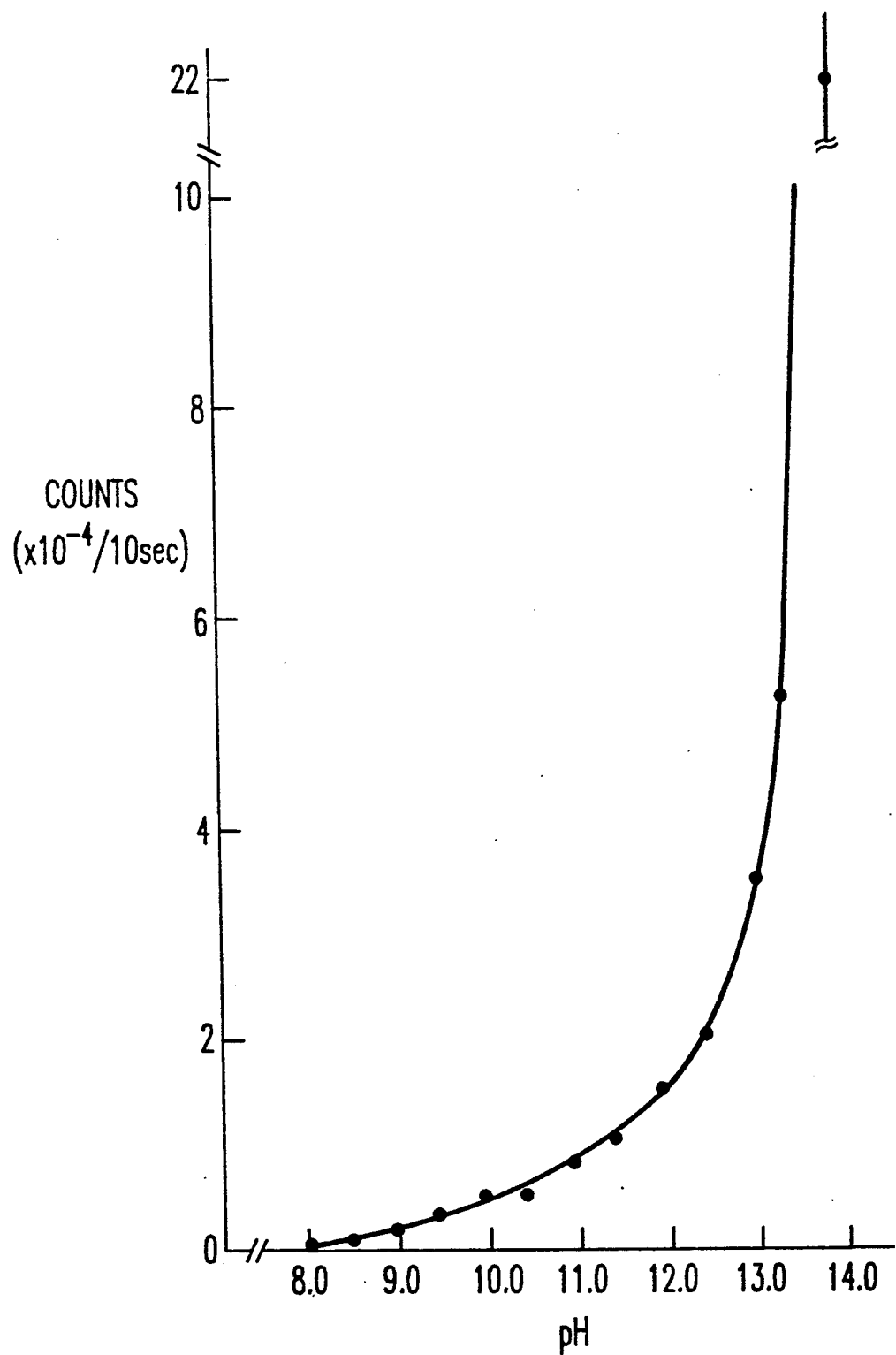
FIG. 1 shows a plot of the light produced in an immunoassay for TSH as a function of the final pH of the reaction mixture after adding alkali, wherein 3-(2'-spiroadamantane)-4-methoxy-4-(3''-phosphoryloxy) phenyl-1,2-dioxetane salt ("AMPPD") is the reporter molecule and wherein alkaline phosphatase is used to cleave and thereby activate the AMPPD.
Figure 2:
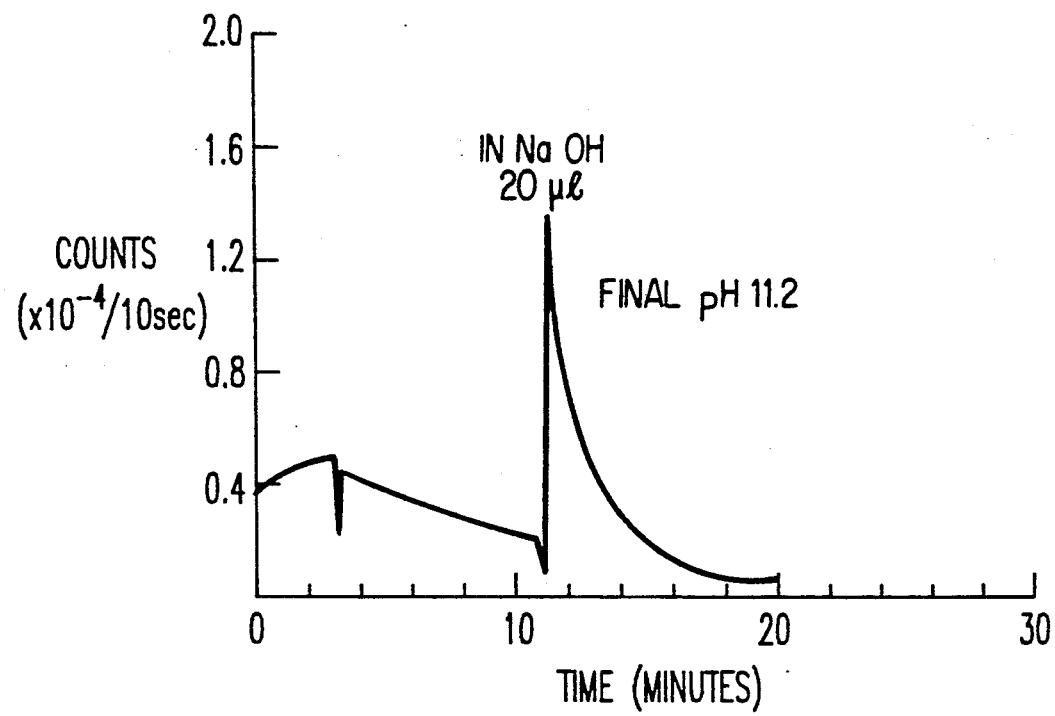
FIG. 2 shows a plot of the light produced in an immunoassay for TSH as a function of time after stopping enzyme catalysis with the heavy metal chelator EDTA, and producing further light by the addition of alkali, wherein AMPPD is the reporter molecule and alkaline phosphatase is used to cleave and thereby activate the AMPPD.

The method of this invention comprises carrying out a first light-producing enzyme-catalyzed cleavage of an enzyme-cleavable dioxetane derivative within a pH range at which enzyme catalysis is most efficient, and thereafter carrying out a second light-producing reaction under strongly alkaline conditions at which light production from the products of the first enzyme-catalyzed reaction is maximum, and the duration of the glow produced is extended.

The method of this invention is applicable to any chemiluminescence-based assay in which the light-producing composition is an enzyme-cleavable 1,2-dioxetane such as the enzymatically-cleavable, water-soluble 1,2-dioxetanes disclosed in Bronstein, WO 88/00695; Schaap, et al. EPO 254,051; and Schaap, et al. (1987).

These 1,2-dioxetanes can be represented by the general formula:

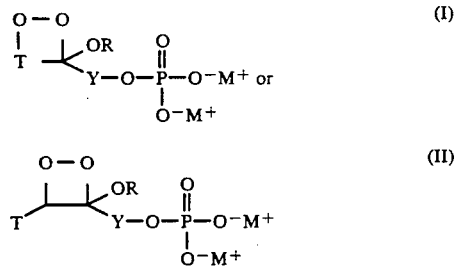

In this formula T is a stability-providing, fused or unfused cycloalkyl, cycloalkylidene or polycycloalkylidene group bonded to the 3-carbon of the dioxetane ring carbon atoms, inclusive, e.g., an adamantyl or adamant-2-ylidene group.

The symbol R represents a lower alkyl group such as methyl, ethyl, propyl or butyl.

The symbol Y represents an aromatic light-emitting fluorophore-forming fluorescent chromophore group capable of absorbing energy to form an excited energy state from which it emits optically detectable energy to return to its original energy state. Preferably, Y represents a group such as a phenyl, naphthyl or anthranyl. $M^+$ is a phosphate-neutralizing cation such as an alkali metal (e.g., $Na^+$, $K^+$), $NH_4^-$ or unsubstituted or alkyl or aralkyl substituted quaternary ammonium cation. The phosphate group is cleavable from the aromatic Y group by an alkaline or acid phosphatase. Such phosphatases can be isolated and purified from animal or plant sources by methods well known in the art, and commercially-available products may, of course, also be used.

If an acid phosphatase is used as the enzyme in the first light-producing enzymatic stage of the reaction, this stage will preferably be performed at a pH from about 4 to about 7. If an alkaline phosphatase is used as the enzyme, this stage will preferably be performed at a pH from about 7 to about 10.5. In other words, the enzymatic reaction will be performed in an optimal pH range for the kind of phosphatase used, i.e., that pH range within which the enzyme has maximum specific activity and stability as determined by standard methods well known in the art of enzymology. Of course, in certain instances it may be preferred to run the enzymatic stage of the assay method at a pH value that is not the optimal pH value. It is necessary only that the enzyme activity at that pH is sufficient to bring the reaction to completion within a length of time that is useful in biochemical assays.

The second stage of the assay method of this invention is carried out under strongly alkaline conditions to induce maximal chemiluminescence. Whether or not the enzymatic reaction of the first stage of these assay methods has gone to substantial completion is related to the degree of reaction of the substrate, and this is accomplished by taking into account such factors as the interrelationship between the amount of enzyme present and the amount of substrate used; this can be determined by methods routine in the art of enzymology.

The enzymatic reaction may be terminated at any point by adding a stopping agent. By the expression "terminated at any point" is meant adding a stopping reagent either during the course of the enzyme-catalyzed stage of the assay method or after the enzyme-catalyzed reaction has gone to substantial completion. Useful stopping agents include enzyme inhibitors such as a chelator (e.g., EDTA and EGTA), organic phosphoric acid esters (e.g., phenyl phosphate and naphthyl phosphate), and inorganic acids (e.g., orthophosphoric acid). Such stopping agents are preferably used in amounts at least ten times their Ki (inhibition constant) value; for example, EDTA is used at a concentration of at least 1 mM, and phenylphosphate is used at a concentration of at least 30 mM.

When an alkaline phosphatase is used as the enzyme, the reaction can be stopped by acidifying the reaction mixture to a pH value below about 7.0, and enzymic catalysis can be resumed, if desired, by readjusting the pH conditions to the above-stated optimal range for the alkaline phosphatase.

The second stage of the assay method of this invention is performed under strongly alkaline conditions, and the total chemiluminescence produced is measured. "Strongly alkaline conditions" means pH values of about 11 and above, which can be attained by adding compounds having hydroxide ions to the reaction system. Suitable compounds for this purpose include hydroxides of alkali metals and alkaline earth metals, such as NaOH, KOH and $Mg(OH)_2$. Ammonium hydroxide or an amine such as ethanolamine can also be used for this purpose.

Maximum light production from the enzyme-activated dioxetane is initiated as soon as the reaction conditions are adjusted to strongly alkaline pH values. The amount of light produced can be readily measured with a commercial luminometer.

The alkaline luminescent reaction can be quenched by dropping the pH to below about 10.5, and, preferably to a neutral or acidic pH, and may be resumed by reestablishing strongly alkaline pH values. In other words, the light-producing reaction can be turned on and off by controlling the pH conditions.

The second-stage light-producing reaction carried out under alkaline conditions may be performed in the presence of a light enhancer substance, such as mammalian serum albumin, a polyalkyl quaternary amine, fluorescein, or dimethyl sulfoxide. Such enhancers are typically used in amounts of 0.0001–10 wt% of the chemiluminescence reaction system.

The method of this invention can be employed to perform an enzyme-based immunoassay. Antigens that can be assayed include drugs, hormones and various disease-related trace components in sera and urine. Suitable antibodies may be formed in warm-blooded animals such as rabbit, goat, horse, guinea pigs and chicks by injecting about 0.3-2 mg per kg of body weight of an antigenic ligand or enzyme one to several times under the dorsal skin, into foot pads, into the femoral muscle, etc., together with a adjuvant. The antibodies produced may be used after fragmentation into F(ab')$_2$, Fab', Fab, etc., moieties with proteolytic enzymes.

Antibodies may also be obtained as monoclonal antibodies by art-recognized methods. Generally, in this case an antigenic ligand or enzyme is injected intraperitoneally or by some other route into a mouse together with an adjuvant, and the spleen cells recovered are fused with mouse myeloma cells using polyethylene glycol. Positive hybridoma cells are selected by cloning, and the monoclonal cells thus selected are grown within the peritoneal cavity of a mouse to obtain a desired monoclonal antibody.

Various methods of immunoassay are described in "Koso Meneki Sokuteiho (Methods of Enzyme Immunoassay)" published by Igaku Shoin in 1987, and a typical example that can be used comprises reacting an antigen with an immobilizing antibody, then reacting an enzyme-labeled antibody with the antigen, and measuring the reaction product.

The method of this invention can also be used in polynucleotide measurements. Various methods of polynucleotide measurements are described in "Molecular and Cellular Probes", vol. 1, p. 177 ff. (1987). In a typical method, the DNA of a specimen immobilized on a nitrocellulose filter is reacted with a hapten-labeled complementary probe DNA, and an anti-hapten antibody bound to alkaline phosphatase is allowed to act on the reaction product. The activity of alkaline phosphatase may be assayed by using a dioxetane derivative as a substrate and applying the multi-pH assay methods described herein above.

The multi-pH method of the invention is applicable to all assay formats, including solid phase formats. In the solid phase format, just as in a soluble state format, the enzyme-catalyzed first light-producing phase of the assay is carried out at pH values optimal for the enzyme, e.g., pH of about 4 to about 7 when using an acid phosphatase and pH of about 7 to about 10.5 when using an alkaline phosphatase and a dioxetane derivative of the general formulae (I) and (II) as substrate. Thereafter, the components bound to a solid matrix are subjected to the second, maximum light-producing alkaline conditions.

The term "solid phase" as used herein is intended to mean a solid matrix material that is incorporated into an assay system as an adsorbent of one or more components of the reaction mixture. It is exemplified by antibodies bound to a solid state to be used in immunoassays, as shown in the examples below. Any solid material may be used as the solid phase, and its shape is not limited in any way Preferred solid phase materials are polymers, such as polystyrene, polyfluoroethylene, nylon, polyacetal and cellulose, or derivatives thereof.

As noted above, after the enzyme-catalyzed phase of the solid phase assay is carried out with a pH range optimal for the enzyme, the second, maximal light-producing alkaline phase of the assay is carried out on the solid phase. The expression "solid phase" should be taken to mean the solid material that remains after removing the soluble phase of the reaction mixture. The term "alkaline conditions" as used herein for solid phase assays means pH values of at least about 11. Such alkaline conditions for solid state assays can be attained by adding to the solid phase the above-mentioned compounds having hydroxide ions, such as hydroxides of alkali metals and alkaline earth metals such as NaOH, KOH and Mg(OH)$_2$, as well as ammonium hydroxide or amines such as ethanolamine, or the like.

The following examples are intended to illustrate the invention in detail, but they are in no way to be taken as limiting, and the present invention is intended to encompass modifications and variations of these examples within the framework of their contents.

EXAMPLE 1

TSH Measurement

A sample containing 15 µl of TSH (0.2 µU/ml) was mixed with 135 µl of an anti-TSH Fab'-bound alkaline phosphatase conjugate (conjugate concentration, 0.5 µg/ml; 0.1 M Tris-HCl; 2% BSA; 1 mM MgCl$_2$; 0.1 mM ZnCl$_2$; pH, 7.5). To the mixture, a polystyrene bead (diameter ⅛ inch) coated with anti-TSH mouse IgG was added and left to stand at room temperature for 2 hr. After washing the bead with distilled water three times, 200 µl of a substrate solution (0.1 M Tris-HCl; 1 mM MgCl$_2$; 0.1 mM ZnCl$_2$, pH, 9.8) containing 100 µg/ml of 3-(2'-spiroadamantan)-4-methoxy-4-(3''-phosphoryloxy)penyl-1,2-dioxetane disodium salt (AMPPD) having the structural formula (III) noted below:

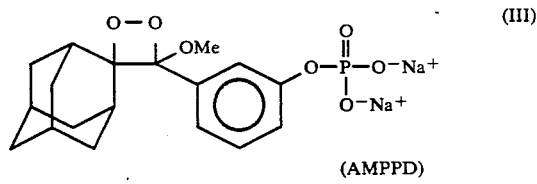

(AMPPD)

was added and left to stand at room temperature for 20 minutes. Both before and immediately after adding various amounts of a solution of sodium hydroxide to the activated AMPPD-containing reaction mixture, the quantity of light produced was determined with a luminometer (Berthold, Inc.); a 10-second integral was taken. The results shown in FIG. 1 demonstrate almost a 100-fold increase in light-energy production by raising the pH of the assay reaction mixture from about 9.8 to 14.

EXAMPLE 2

A sample containing 15 µl of TSH (0.40 µU/ml) was mixed with 135 µl of an anti-TSH Fab'-bound alkaline phosphatase conjugate (conjugate concentration 0.5 µg/ml, 0.1 M Tris-HCl, 2% BSA, 1 mM MgCl$_2$, 0.1 mM ZnCl$_2$, pH, 7.5). To the mixture, a polystyrene bead (diameter ⅛ inch) coated with anti-TSH mouse IgG was added and left to stand at room temperature for 2 hours After washing the bead with distilled water three times, 200 µl of a substrate solution (0.1 M Tris-HCl,, 1 mM MgCl$_2$, 0.2 mM ZnCl$_2$, pH 9.8) containing 100 µg/ml of AMPPD was added and left to stand for reaction at room temperature.

After a 15-minute reaction period, the light produced was measured with a luminometer (Berthold, Inc.). At various times thereafter, 100 µl of a solution (0.1 M Tris-HCl, 0.2 M Na$_2$HPO$_4$, 10 mM EDTA, pH 9.8) was added to quench the enzymatic reaction. Eight minutes after the addition of the stopping solution, 20 µl of 1N NaOH was added to elevate the pH of the reaction solution to 11.2. The quantity of light produced was determined with a luminometer; a 10-second integral was taken. The results shown in FIG. demonstrate that inhibiting the enzymatic phase of the reaction by the addition of EDTA reduced light production by about 50%, and bringing the pH to 11.2 increased light production by about 6-fold.

EXAMPLE 3

A sample containing 15 μl of TSH (0.40 μU/ml) was mixed with 135 μl of an anti-TSH Fab'-bound alkaline phosphatase conjugate (conjugate concentration 0.5 μg/ml, 0.1 M Tris-HCl, 2% BSA, 1 mM MgCl$_2$, 0.1 mM ZnCl$_2$, pH 7.5). To the mixture, a polystyrene bead (diameter ⅛ inch) coated with anti-TSH mouse IgG was added, and left to stand at room temperature for 2 hours. After washing the bead with distilled water three times, 200 μl of a substrate solution (0.1 M Tris-HCl, 1 mM MgCl$_2$, 0.1 mM ZnCl$_2$, pH 9.8) containing 100 μg/ml of AMPPD was added and left to stand for reaction at room temperature.

Figure 3:
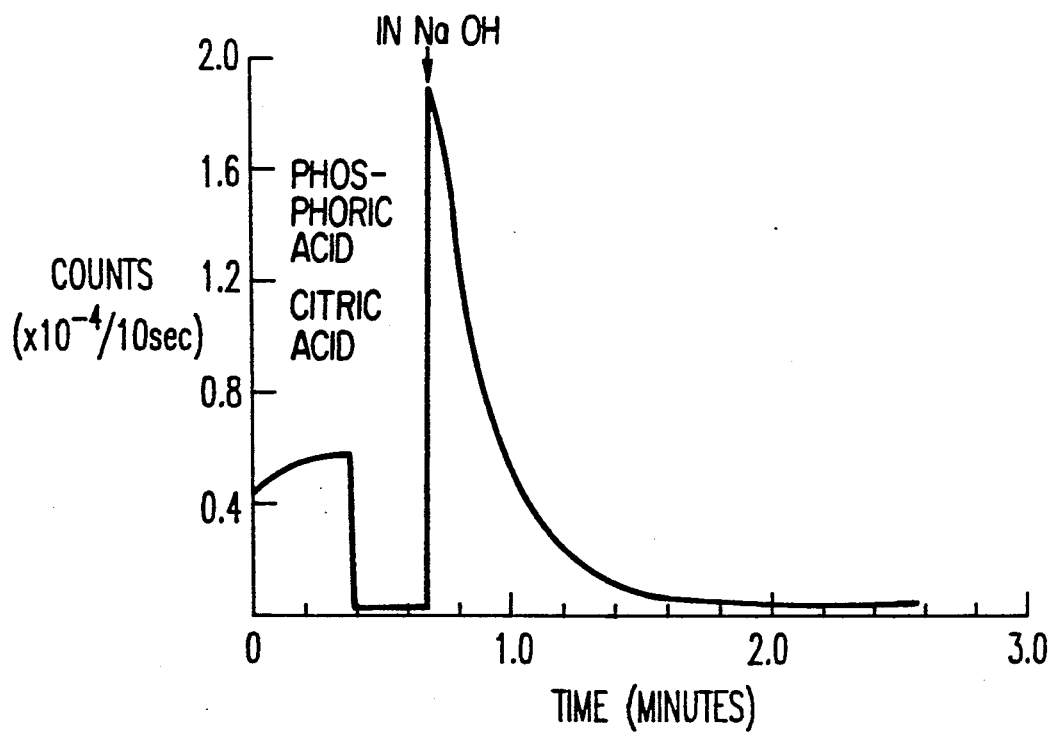
FIG. 3 shows a plot of light produced in an immunoassay for TSH as a function of time after stopping enzyme catalysis with an acid, and thereafter producing light by the addition of alkali, wherein AMPPD is the reporter molecule and alkaline phosphatase is used to cleave and thereby activate the AMPPD.

After 40 minutes of reaction, a light measurement was made with a luminometer (Berthold, Inc.). At various times thereafter, 200 μl of a 0.1 M phosphoric acid-citric acid solution (pH 3.0) was added to lower the pH of the reaction 15 solution to 4.6. Three minutes later, 50 μl of 1N NaOH was added to raise the pH of the reaction solution to 12.0. The quantity of luminescence produced was counted with the luminometer, and a 10-second integral was taken. The results shown in FIG. 3 demonstrate that dropping the pH to 4.6 reduced light production virtually 100%, and that adding alkali thereafter produced a great increase in light energy.

EXAMPLE 4

Effect of Dimethyl Sulfoxide (DMSO) as a Light Enhancer Substance on an Assay for TSH A sample containing 15 μl of TSH (0.2 μU/ml) was mixed with 135 μl of an anti-TSH Fab'-bound alkaline phosphatase conjugate (conjugate concentration 0.5 μg/ml, 0.1 M Tris-HCl, 2% BSA, 1 mM MgCl$_2$, 0.1 mM ZnCl$_2$, pH 7.5). To the mixture, a polystyrene bead (diameter ⅛ inch) coated with anti-TSH mouse IgG was added, and left to stand at room temperature for 2 hr. After washing the bead with distilled water three times, 200 μl of a substrate solution (0.1 M Tris-HCl, 1 mM MgCl$_2$, 0.1 mM ZnCl$_2$, pH 9.8) containing 100 g/ml of AMPPD was added to the bead and the mixture was incubated at room temperature.

Thereafter, 100 μl of 2N NaOH or a mixture of 2N NaOH and DMSO (2N NaOH to DMSO ratio, 2:1, 1:1, or 1:2) were added to the reaction solution, and the quantity of light produced determined with a luminometer (Berthold, Inc.); a 10-second integral was taken. The results are shown in Table 1 below.

TABLE I

| DMSO % | Light Count/10 sec | Relative Light Count |
|---|---|---|
| 0 | 41,100 | 1.0 |
| 33 | 75,000 | 1.8 |
| 50 | 82,000 | 4.4 |
| 66 | 549,600 | 13.4 |

All concentrations of DMSO studied greatly enhanced light production over that produced by alkali alone.

EXAMPLE 5

ELISA Assay for Alphafetoprotein (AFP) in the Presence of a Quaternary Amine

A sample containing 10 μl of AFP (0, 10, 50 ng/ml) was mixed with 150 μl of an anti-AFP Fab'-bound alkaline phosphatase conjugate (conjugate concentration 0.5 μg/ml, 0.1 M Tris-HCl, 2% BSA, 1 mM MgCl$_2$, 0.1 mM ZnCl$_2$, pH 7.5). To the mixture, a polystyrene bead (diameter ⅛ inch) coated with anti-AFP mouse IgG was added and left to stand at room temperature for 30 min. After washing the bead with distilled water three times, 200 μl of a substrate solution (0.1 M Tris-HCl, 1 mM MgCl$_2$, 0.1 mM ZnCl$_2$, pH 9.8) containing 100 μg/ml AMPPD without or with 0.05% polydiaryl dimethyl ammonium chloride (PDDAC) wa added; the mixture was reacted at room temperature for 20 minutes. The quantity of light produced was determined with a luminometer (Berthold, Inc.) and a 10-second integral was taken. The results are shown in Table 2 below.

TABLE 2

| PDDAC (%) | Light Count/10 sec | Relative Light Count |
|---|---|---|
| 0 | 12,390 | 1 |
| 0.05 | 96,050 | 7.8 |

The amount of PDDAC used produced almost an 8-fold enhancement in light production.

EXAMPLE 6

Effect of the Frequency of Washing the Solid Phase on TSH Measurement

Figure 4:
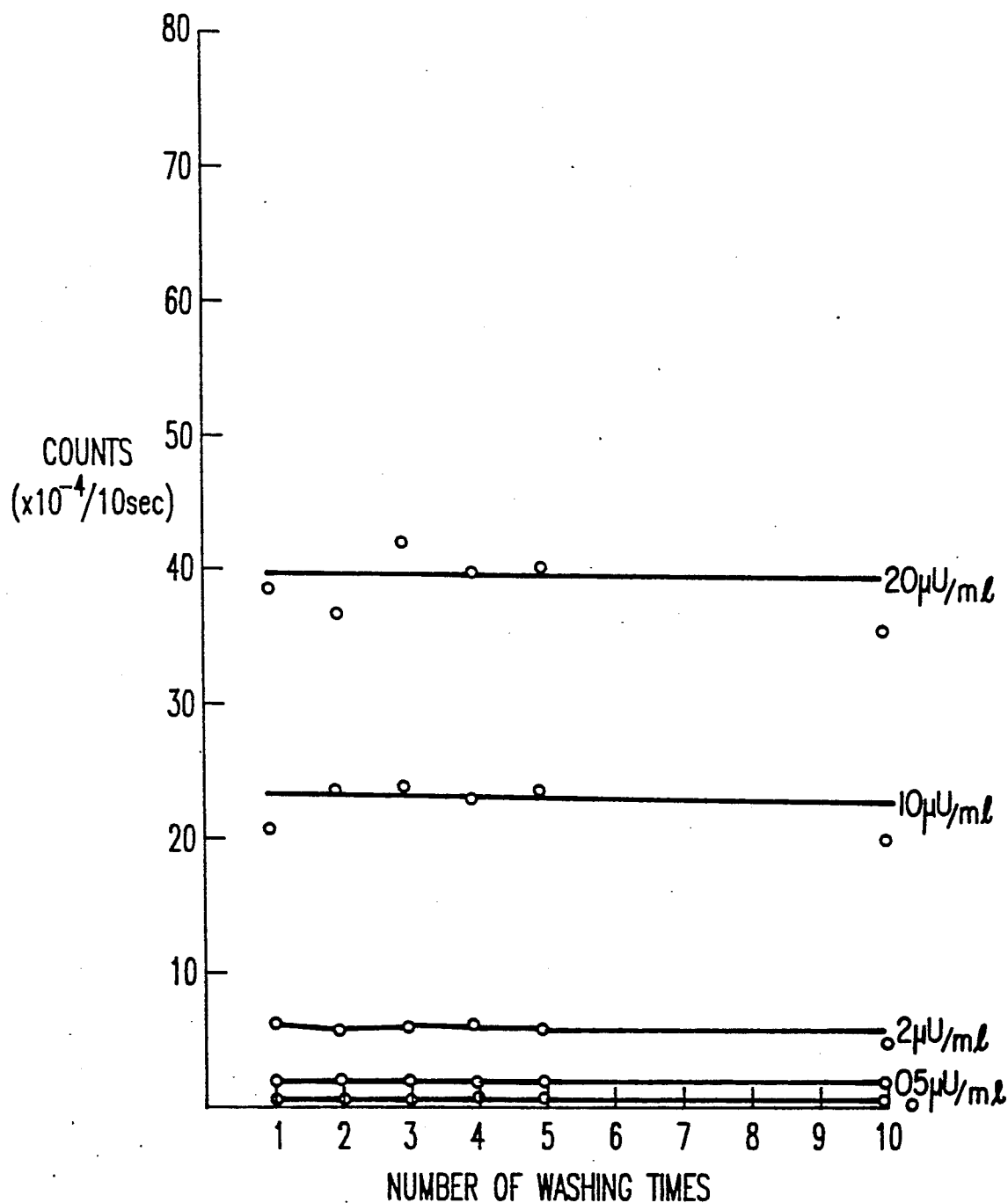
FIG. 4 shows the effect of multiple washings of the solid phase on the light levels produced in the chemiluminescence-based multi-pH assay method for TSH illustrated in FIG. 1.

A sample containing 20 μl of TSH (0, 0.5, 2, 10, 20 μU/ml) was mixed with 300 μl of an anti-TSH Fab'-bound alkaline phosphatase conjugate (conjugate concentration 0.5 μg/ml, 0.1 M Tris-HC, 2% BSA, 1 mM MgCl$_2$, 0.1 mM ZnCl$_2$, pH 7.5). To the mixture, a polystyrene bead (diameter 1/4 inch) coated with anti-TSH mouse IgG was added and left to stand at room temperature for 2 hr. After washing the bead with distilled water three times, 200 μl of a substrate solution (0.1 M Tris-HCl, 1 mM MgCl$_2$, 0.1 mM ZnCl$_2$, pH 9.8) containing 100 μg/ml of AMPPD was added and left to react at room temperature for 20 min.. Thereafter, the bead was washed from 1 to 10 times with 2 ml of distilled water. Immediately upon addition of 300 μl of 4N NaOH (pH 13.5), the quantity of light produced was determined with a luminometer (Berthold, Inc.), and a 10-second integral was taken. The results shown in FIG. 4 demonstrate that bead-bound, light-producing dioxetane products were not removed by repetitive washing.

EXAMPLE 7

AFP measurement by ELISA Using Various Polymer Beads

Samples containing 20 μl of AFP (1 ng/ml) were each mixed with 300 μl of an anti-AFP Fab'-bound alkaline phosphatase conjugate (conjugate concentration 0.5 g/ml, 0.1 M Tris-HCl, 2% BSA, 1 mM MgCl$_2$, 0.1 mM ZnCl$_2$, pH 7.5). To each mixture, a polymer bead (for the name of polymer and the bead diameter, see Table 3) coated with anti-AFP mouse IgG was added and left to stand at room temperature for 2 hr. After washing the bead with distilled water three times, 200 μl of a substrate solution (0.1 M Tris-HCl, 1 mM MgCl$_2$, 0.1 mM ZnCl$_2$, pH 9.8) containing 10 μg/ml of AMPPD was added and reacted at room temperature for 20 minutes. The bead was again washed with distilled water three times. Immediately after adding 300 μl of 4N NaOH and 10 μl of distilled water, the quantity of light produced was determined with a luminometer (Berthold, Inc.) and a 100-second integral (B) was taken. As a control, a 100-second integral (A) was taken for the sample to which only distilled water was added instead of 4N NaOH. The amplification factor for each type of polymer bead was determined and the results are shown in Table 3 below. The results indicate that polystyrene beads produced the greatest amplification of light production.

TABLE 3

| Bead | Counts (A) | Counts (B) | Amplification factor (A)/(B) |
|---|---|---|---|
| Polystyrene | | | |
| ⅛ inch Meiwa #80 | 950 | 12,830 | 13.5 |
| #280 | 1090 | 26,710 | 25.5 |
| #0 | 890 | 5,990 | 6.7 |
| Sekisui #280 | 1150 | 67,650 | 58.8 |
| ⅛ inch Meiwa #80 | 240 | 7,260 | 30.3 |
| Polyfluorethylene | | | |
| ⅛ inch #80 | 910 | 5,020 | 5.5 |
| Polyacrylonitrile | | | |
| ⅛ inch #0 | 790 | 1,130 | 1.4 |
| Duracon polycetal | | | |
| ⅛ inch #0 | 880 | 2,290 | 2.6 |
| Polymethylpentene | | | |
| ⅛ inch #0 | 880 | 2,470 | 2.8 |

The present invention provides a method of chemiluminescence assay that combines light production by an enzymatic reaction at the optimal pH for enzyme activity with light production from an activated and decomposed dioxetane substrated under strongly alkaline conditions. This method yields quantities of luminescence sufficient to prove high-sensitivity and high-precision measurements. The utility of this method is further enhanced by its capability of controlling the timing of luminescence.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. In a method of conducting a chemiluminescence-based assay in an aqueous environment in the presence of a stabilized chemiluminescent dioxetane derivative having as the substrate an enzyme cleavable substituent of the formula:

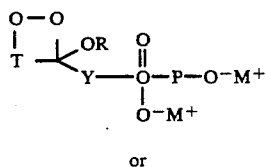

or

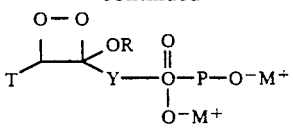

where T is a spiro-linked or non-spiro-linked adamantine moiety, R is a lower alkyl group, Y is an aromatic group, M+ is a proton or a cation, and the phosphate group is enzyme cleavable, wherein the substrate is cleaved by a phosphatase enzyme capable of cleaving the phosphate substituent to generate visible light in the form of a sustained glow which is detectable by a light detection means, and the visible light generated is detected, wherein the improvement comprises (a) cleaving the phosophate ester substituent from the dioxetane by adding said phosphatase to said dioxetane at a pH at which said phosphatase has maximum specific activity and stability, (b) allowing the enzyme-catalyzed cleavage reaction to go to substantial completion and (c) adjusting the pH of the reaction mixture to a strongly alkaline pH optimal for the generation of visible light from the products of the cleavage reaction.

2. A method of claim 1 wherein the enzyme is an acid phosphatase and pH range for the enzyme-catalyzed step if from about 4 to about 7.

3. A method of claim 1 wherein the enzyme is an alkaline phosphatase, and the pH range for the enzyme-catalyzed step is from about 7 to about 10.5.

4. A method of claim 1 which is used in an immunoassay.

5. A method of claim 1 which is used in a polynucleotide assay comprising reacting a DNA specimen with a hapten-labeled complementary probe DNA, and adding thereto alkaline phosphatase bound to an anti-hapten antibody, allowing said antibody to bind to said hapten-labeled probe, adding said dioxetane to said mixture, and allowing said cleaving reaction to go forward as recited in claim 1, wherein cleavage of said dioxetane phosphate by said alkaline phosphatase to produce visible light enables the detection of said polynucleotide by said complimentary probe.

6. A method of any one of claims 1-5 wherein said cleavage reaction is stopped prior to substantial completion by adding to said reaction mixture an enzyme stopping reagent before adjusting the reaction mixture to a pH of at least about 11.

7. A method of claim 6 wherein the stopping reagent is an enzyme inhibitor selected from the group consisting of a chelator, organic phosphoric acid esters, inorganic acids and mixtures thereof.

8. A method of any one of claim 1-5 wherein a light-enhancing compound selected from the group consisting of mammalian serum albumin, a polyalkyl quaternary amine, fluorescein, dimethylsulfoxide and mixtures thereof is present after the pH of the reaction mixture has been adjusted to at least about 11.

9. A method of claim 4 carried out as a solid-phase assay comprising combining, as a reaction mixture, an analyte suspected of comprising an antigen, an antibody to said antigen bound to alkaline phosphatase and a solid to which is bound an antibody to said antigen, washing said solid, and adding thereto said dioxetane, and conducting the process as recited in claim 1.

10. A method of claim 9 wherein said solid phase is polystyrene, polyfluoroethylene, nylon or polyacetal.

11. A method of claim 9 wherein a light-enhancing compound selected from the group consisting of mammalian serum albumin, a polyalkyl quaternary amine, fluorescein, dimethylsulfoxide and mixtures thereof is present after the pH of the reaction mixture has been adjusted to at least about 11.

* * * * *